(12) United States Patent
Sandhu

(10) Patent No.: US 8,377,708 B2
(45) Date of Patent: *Feb. 19, 2013

(54) REACTION APPARATUS AND PROCESS

(75) Inventor: Adarsh Sandhu, Tokyo (JP)

(73) Assignee: Empire Technology Development LLC, Wilmington, DE (US)

( * ) Notice: Subject to any disclaimer, the term of this patent is extended or adjusted under 35 U.S.C. 154(b) by 76 days.

This patent is subject to a terminal disclaimer.

(21) Appl. No.: 12/665,704

(22) PCT Filed: Jul. 31, 2008

(86) PCT No.: PCT/JP2008/063750
§ 371 (c)(1),
(2), (4) Date: Apr. 14, 2010

(87) PCT Pub. No.: WO2010/013337
PCT Pub. Date: Feb. 4, 2010

(65) Prior Publication Data
US 2011/0076777 A1    Mar. 31, 2011

(51) Int. Cl.
*G01N 25/08* (2006.01)
(52) U.S. Cl. ............ 436/150; 436/514; 436/526; 422/50
(58) Field of Classification Search .................. None
See application file for complete search history.

(56) References Cited

U.S. PATENT DOCUMENTS

| | | | |
|---|---|---|---|
| 4,911,555 A * | 3/1990 | Saffer et al. .................. 366/274 |
| 6,764,859 B1 | 7/2004 | Kreuwel et al. | |
| 7,396,690 B2 | 7/2008 | Colin | |
| 2002/0086325 A1 | 7/2002 | Nagasawa | |
| 2003/0134316 A1 | 7/2003 | Tashiro et al. | |
| 2008/0073545 A1 | 3/2008 | Akashi et al. | |
| 2008/0191688 A1 | 8/2008 | Kahlman et al. | |

FOREIGN PATENT DOCUMENTS

JP    52-100657    8/1977

(Continued)

OTHER PUBLICATIONS

International Search Report for PCT/JP2008/063586 mailed Oct. 7, 2008.
International Search Report for PCT/JP2008/063743 mailed Oct. 7, 2008.

(Continued)

*Primary Examiner* — Robert Xu
(74) *Attorney, Agent, or Firm* — Foley & Lardner LLP

(57) ABSTRACT

A new reaction apparatus including a capillary having an inner surface to which a probe molecule that specifically binds to an analyte is immobilized and achieving a highly efficient reaction using a small amount of a sample and a process of the reaction are provided. The reaction apparatus includes a capillary having an inner surface to which a probe molecule that specifically binds to an analyte is immobilized; a passage allowing a fluid discharged from one end of the capillary to flow to the other end of the capillary; a columnar magnetic body that is disposed in a fluid containing the analyte in the capillary and/or the passage in the state that the fluid fed in the capillary can circulate via the passage; end-fixing means for fixing one end of the columnar magnetic body in the capillary and/or the passage by a DC magnetic field; and end-moving means for moving the other end of the columnar magnetic body by an AC magnetic field such that the fluid circulates via the passage.

6 Claims, 5 Drawing Sheets

(A)

(B)

FOREIGN PATENT DOCUMENTS

| | | |
|---|---|---|
| JP | 58-210863 | 12/1983 |
| JP | 60-001793 | 1/1985 |
| JP | 62-247382 | 10/1987 |
| JP | 2002-202305 | 7/2002 |
| JP | 2003-504195 | 2/2003 |
| JP | 2003-248008 | 9/2003 |
| JP | 2004-534243 | 11/2004 |
| JP | 2007-187602 | 7/2007 |
| JP | 2007-319735 | 12/2007 |
| JP | 2008-012490 | 1/2008 |
| WO | WO 2006/079998 | 8/2006 |
| WO | WO 2008/004550 | 1/2008 |

OTHER PUBLICATIONS

International Search Report for PCT/JP2008/063744 mailed Oct. 7, 2008.
International Search Report for PCT/JP2008/063750 mailed Oct. 7, 2008.
Doyle, P. S. et al., "Self-Assembled Magnetic Matrices for DNA Separation Chips," *Science*, vol. 295, Mar. 22, 2002, pp. 2237.
Liu, J. et al., "Field-Induced Structures in Ferrofluid Emulsions," *Physical Review Letters*, vol. 74, No. 14, Apr. 3, 1995, pp. 2828-2831.
Non-Final Office Action for U.S. Appl. No. 12/665,710, mailed on Sep. 26, 2011, 8 pp.

\* cited by examiner (A)

(B)

(A)　　　　　　　　　　　(B)

(C)

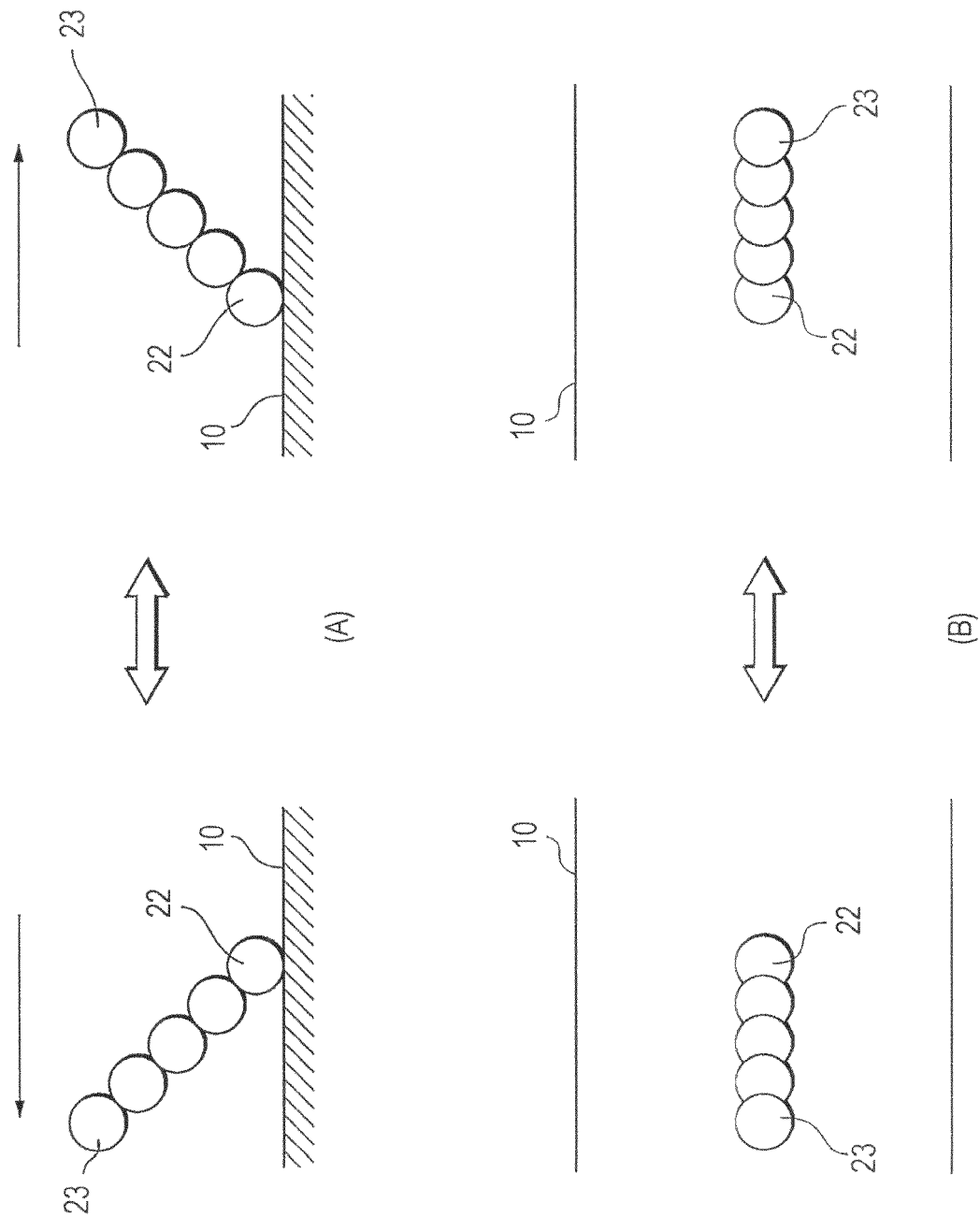

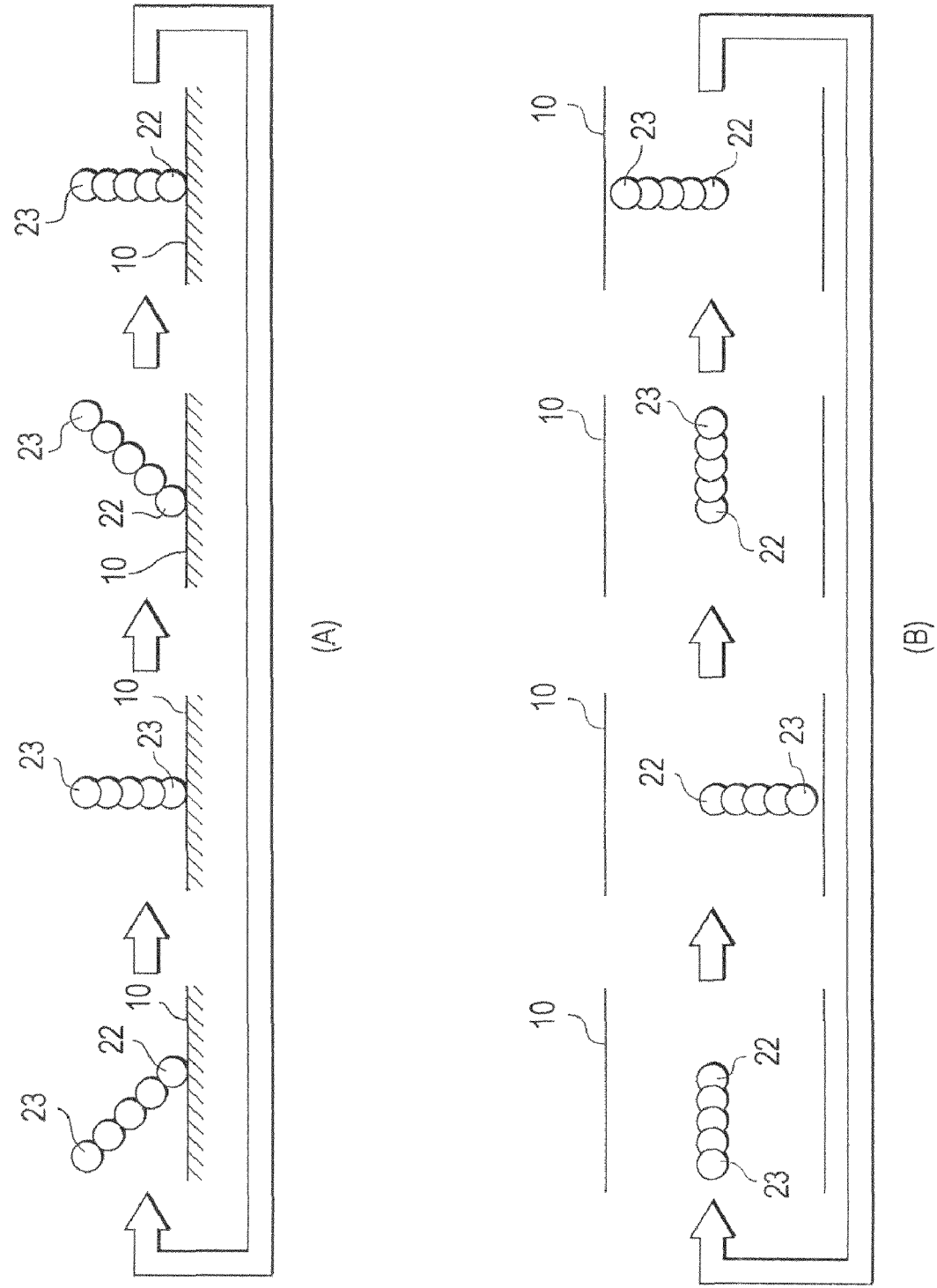

REACTION APPARATUS AND PROCESS

CROSS-REFERENCE TO RELATED APPLICATIONS

The present application is a US. national stage application claiming the benefit of International Application No. PCT/JP2008/063750, filed on Jul. 31, 2008, the entire content of which is incorporated herein by reference in its entirety.

TECHNICAL FIELD

The present invention relates to a reaction apparatus including a capillary having an inner surface to which a probe molecule that specifically binds to an analyte is immobilized, and relates to a process of the reaction.

BACKGROUND ART

Reaction apparatuses utilizing affinity detection, which uses a substance that selectively binds to a specific molecule for selectively detecting a substance that corresponds to the molecule, have been developed. For example, Japanese Unexamined Patent Application Publication No. 2002-202305 (Patent Document 1) discloses an affinity detection/analysis chip having a structure in which a plurality of capillaries having inner surfaces to which a probe molecule that specifically binds to an analyte to be detected is immobilized are bundled and discloses a detection system.

Specifically, in the detection system disclosed in Patent Document 1, a sample to be analyzed is allowed to flow in the plurality of capillaries so that an analyte molecule contained in the sample binds to the capillary inner surfaces through a specific bond between the analyte molecule and the probe molecule. The bond formed in the insides of the capillaries is observed and analyzed using a light absorption observation device.

DISCLOSURE OF INVENTION

Problems to be Solved by the Invention

When a reaction apparatus for binding (immobilizing) an analyte is thus configured with capillaries having inner surfaces to which a probe molecule that specifically binds to the analyte is immobilized, a common pump, such as a syringe pump or a piston pump, is necessarily provided at the outside of the capillary for allowing a fluid (sample) containing the analyte to flow into the insides of the capillaries.

However, since the apparent viscosity of a fluid flowing in the microscopic passage of a capillary is significantly high, it is difficult for a common pump to precisely control the transfer of a fluid sample present at any position (in particular, at a position far from the pump) in a passage. Consequently, the throughput time for completing the binding reaction may become longer.

In addition, the fluid sample has to have a volume at least for flowing in the piping such as the inside of a pump. This also causes the problem that the efficiency of sample use is reduced.

Furthermore, in the conventional structure, for example, when the amount of an analyte molecule to be detected that is contained in a sample is small, in order to allow the analyte molecule to sufficiently bind to a probe molecule on a capillary inner surface, the binding opportunity has to be increased by increasing the volume of the sample flowing in the capillary, resulting in the problem that a large amount of a sample is necessary.

Accordingly, the present invention has been accomplished under these circumstances, and it is an object thereof to provide a new reaction apparatus including a capillary having an inner surface to which a probe molecule that specifically binds to an analyte is immobilized, allowing a short throughput time for completing the binding reaction, and achieving a highly efficient reaction using a small amount of a sample and to provide a process of the reaction.

Means for Solving the Problems

A reaction apparatus of the present invention includes a capillary having an inner surface to which a probe molecule that specifically binds to an analyte is immobilized; a passage allowing a fluid discharged from one end of the capillary to flow to the other end of the capillary; a columnar magnetic body that is disposed in a fluid containing the analyte in the capillary and/or the passage in the state that the fluid placed in the capillary can circulate via the passage; end-fixing means for fixing one end of the columnar magnetic body in the capillary and/or the passage using a DC magnetic field; and end-moving means for moving the other end of the columnar magnetic body using an AC magnetic field such that the fluid circulates via the passage.

The end-moving means applies an AC magnetic field in a direction approximately parallel to the fluid transfer direction to allow the other end to reciprocate in the fluid transfer direction and the opposite direction such that the magnetic body moves as a pendulum using the one end as the fulcrum.

The end-moving means can allow the other end to reciprocate at different rates in the outward movement and the homeward movement.

The end-moving means applies an AC magnetic field such that the direction of the magnetic field rotates 360° in a plane containing the capillary or the passage and allows the other end to move approximately in a circle in the plane such that the magnetic body moves such as a conical pendulum using the one end as the fulcrum.

The columnar magnetic body may be formed by magnetically binding a plurality of magnetic particles in a columnar shape by the DC magnetic field.

A reaction process of the present invention includes the steps of, in the state that a fluid containing an analyte is placed in a capillary having an inner surface to which a probe molecule that specifically binds to the analyte is immobilized, fixing one end of a columnar magnetic body disposed in the fluid in the capillary by a DC magnetic field; and moving the other end of the columnar magnetic body by an AC magnetic field such that the fluid circulates via a passage connecting both ends of the capillary.

Advantages

In the reaction apparatus and process of the present invention, though a capillary having an inner surface to which a probe molecule that specifically binds to an analyte is immobilized is used, a highly efficient reaction is possible using a small amount of a sample.

BEST MODES FOR CARRYING OUT THE INVENTION

An embodiment of the present invention will now be described with reference to drawings. FIG. 1(A) is a diagram schematically illustrating a rough structure of a reaction apparatus 1 according to the embodiment of the present invention.

As shown in the drawing, the reaction apparatus 1 includes a microcapillary tube 10 having an inner surface to which a probe molecule 51 that specifically binds to an analyte 50 (for example, a physiologically active substance such as a protein or a DNA) is immobilized and a passage (circulation passage) 11 for connecting both ends of the microcapillary tube 10. In the drawing, one microcapillary tube 10 is shown, but a plurality of microcapillary tubes 10 that is accumulated may be used. In addition, for illustrative purposes, in the drawing, the direction from the left to the right is the X-axis, the direction from the bottom to the top is the Y-axis, and the direction from the front to the back is the Z-axis.

The microcapillary tube 10 can be produced by a known method (for example, Patent Document 1). Specifically, the microcapillary tube 10 can be produced from a vitreous material (silica glass or borosilicate glass), an organic material, a plastic material (polyetheretherketone, polyethylene, or polypropylene), or a carbon nanotube, and the size thereof can be, for example, about 10 to 100 μm in the inner diameter and about 1 to 5 mm in the length.

The passage 11 is a channel for circulating a fluid (for example, a gas, liquid, or gel, which is selected according to a purpose, and hereinafter, referred to as "sample") containing an analyte 50 and is configured such that a sample discharged from one end (outlet end 12) of the microcapillary tube 10 is sent to the other end (inlet end 13). The material of the passage 11 may be any known material such as glass, silicon, or plastic, and the size thereof can be determined according to the size of the microcapillary tube 10.

Furthermore, a feeding channel 14 for feeding a sample into the reaction apparatus 1 is connected near the inlet end 13 of the microcapillary tube 10, and the connection is provided with a valve (not shown) so that the circulating sample does not flow into the feeding channel.

FIG. 1(B) is a diagram schematically illustrating the appearance of the microcapillary tube 10 in the state that a sample is placed in the reaction apparatus 1.

The probe molecule 51 may be any complementary molecule that specifically binds to the analyte 50 and can be properly selected according to the design, as in known techniques. Specifically, the probe molecule 51 can be, for example, a DNA, an RNA, an antigen, an antibody, an enzyme, or a protein, according to the analyte 50.

The probe molecule 51 can be immobilized to the inner surface of the microcapillary tube 10 via a linker, as in known techniques. Exemplary embodiments of the immobilization include that by binding a linker (for example, glutaraldehyde) coupled to the probe molecule 51 to a reactive group (for example, a silanol group) formed on the inner surface of the microcapillary tube 10 and that by binding a linker (for example, succinic acid) to a reactive group present on the inner surface of the microcapillary tube 10 and synthesizing the probe molecule 51 on the linker material.

As shown in FIGS. 1(A) and 1(B), the reaction apparatus 1 of this embodiment further includes magnetic bodies 20 disposed in a sample in the state that the sample is placed in the reaction apparatus 1 (specifically, in the microcapillary tube 10 and the passage 11) and end-fixing means 31 and end-moving means 32 as a controller 30 for controlling the behavior of the magnetic bodies 20.

In addition, in FIG. 1(A), the end-fixing means 31 and the end-moving means 32 are arranged on the Z-axis plus direction side and the Y-axis minus direction side, respectively, with respect to the microcapillary tube 10 in the drawing, but these means may be arranged at any positions that allow application of a DC magnetic field 40 and an AC magnetic fields 41 and 42, which are described below, according to the design.

FIG. 2 schematically shows a structure of the magnetic body 20. As shown in the drawing, the magnetic body 20 is composed of a plurality of magnetic particles 21 that are magnetically bonded in a columnar shape and includes two ends 22 and 23 that corresponds both ends of a column.

One end 22 of the magnetic body 20 is fixed by the end-fixing means 31 so as to be in contact with the microcapillary tube 10, as described below. The other end 23 of the magnetic body 20 is not fixed and is controlled by the end-moving means 32 so as to, for example, reciprocate, as described below.

The magnetic particles 21 can be produced by a known method and may be particles of composite containing a magnetic body, as well as particles of magnetic body itself. The magnetic particles 21 can be in various shapes such as a grain, plate, box, or needle-like shape (for example, magnetic carbon nanotube (CNT)), and the size thereof can be determined according to the size of the microcapillary tube 10, the type of the sample, and the required fluid-transferring and stirring abilities (in the present application, the term "fluid-transferring" is used for transferring not only a liquid sample but also a sample other than a liquid).

The end-fixing means 31 is a device for applying a DC magnetic field 40 to a direction (for example, the Z-axis minus direction in the coordinate system shown in FIG. 1) approximately orthogonal to the tube channel direction of the microcapillary tube 10 (refer to FIG. 3(A)). Such a device can be realized by controlling, for example, a permanent magnet or an electromagnet, with a controller, in conventional methods.

It is known that application of a DC magnetic field to magnetic particles dispersed in a fluid binds the magnetic particles to one another to form a columnar shape having the incident side of the magnetic field as a bottom (for example, refer to "Field-Induced Structures in Ferrofluid Emulsions", PHYSICAL REVIEW LETTERS, Volume 74, Number 14, 3 Apr. 1995 that is incorporated in this application by reference). The distance between the "columns" and the height thereof can be controlled by regulating, for example, the magnitude of the DC magnetic field applied.

The magnetic body 20 in this embodiment is formed by utilizing the above-described phenomenon. That is, the magnetic particles 21 are induced and dispersed in a sample, and then the DC magnetic field 40 is applied to a direction approximately orthogonal to the tube channel direction of the microcapillary tube 10 by the end-fixing means 31 to magnetically bind the magnetic particles 21 to one another into a columnar shape having the bottom (the fixed end 22) on the incident side of the magnetic field of the microcapillary tube 10. As a result, the magnetic body 20 is formed.

Here, the microcapillary tube 10 may be applied with a magnetic particle or a magnetic thin film in advance on the incident side of the magnetic field. The application may be performed by a known method such as adhesion. In such a case, since the magnetic particles 21 are magnetically bound to one another using the magnetic particle or the like applied in advance as the bottom of a column, the position where the magnetic body 20 is formed can be determined in advance.

The end-moving means 32 is a device for applying an AC magnetic field 41 that is approximately parallel to the tube channel direction (the Y-axis direction in the coordinate system shown in FIG. 1) of the microcapillary tube 10 or applying an AC magnetic field 42 such that the direction of the magnetic field rotates 360° in a predetermined plane (for example, the X-Y plane in the coordinate system shown in FIG. 1) (refer to FIGS. 3(B) and 3(C)). This device can be realized by controlling the magnetic field generated by AC current with a controller, as conventionally known.

The end 23 of the magnetic body 20 is not fixed to the microcapillary tube 10 and therefore moves by the influence of the AC magnetic field 41 applied by the end-moving means 32.

In addition, since the end 22 of the magnetic body 20 is also influenced by the AC magnetic field 41 applied by the end-moving means 32, the magnitude of the DC magnetic field 40 applied by the end-fixing means 31 is set to be sufficiently higher than that of the AC magnetic field 41 applied by the end-moving means 32 so that the end 22 is fixed to the microcapillary tube 10 regardless of such influence.

Examples of the reaction process using the reaction apparatus 1 in this embodiment will be specifically described below.

EXAMPLE 1

In Example 1, an increase in reaction efficiency is attempted by using the magnetic body 20 as a nano-pump.

First, the magnetic particles 21 are mixed with a sample containing the analyte 50 and dispersed in the sample (step 1).

Subsequently, the sample including the dispersed magnetic particles 21 is fed into the reaction apparatus 1 (microcapillary tube 10) from the feeding channel (step 2).

Then, a DC magnetic field 40 is applied in a direction approximately orthogonal to the tube channel direction of the microcapillary tube 10 by the end-fixing means 31 (step 3). The DC magnetic field 40 herein is applied in the Z-axis minus direction in the coordinate system shown in FIG. 1.

The application of such DC magnetic field 40 magnetically binds the magnetic particles 21 dispersed in the sample to one another to form a magnetic body 20 having a columnar shape with the bottom (fixed end 22) on the back-side surface (the surface on the Z-axis plus direction side), which is the side that the DC magnetic field enters, of the microcapillary tube 10.

The distance between the magnetic bodies 20 (distance between ends 22) and the height (the binding number of the magnetic particles 21) formed on the back-side surface of the microcapillary tube 10 are determined depending on the diameter, magnetic moment, and type (such as Fe, Co, or Ni) of the magnetic particles 21. Specifically, the distance and the height can be determined according to, for example, the size of the microcapillary tube 10, the type of the sample, the required fluid-transferring and stirring abilities, and the density of the probe molecule 51.

Subsequently, an AC magnetic field 41 is applied by the end-moving means 32 in a fluid-transfer operation mode (step 4). In the fluid-transfer operation mode, the AC magnetic field 41 is applied in a direction approximately parallel to the tube channel direction of the microcapillary tube 10 (the Y-axis direction in the coordinate system shown in FIG. 1). The application of such AC magnetic field 41 allows the end 23 of the magnetic body 20 to reciprocate in the direction of the AC magnetic field 41, namely, in the Y-axis minus direction (the fluid transfer direction) and the Y-axis plus direction (the opposite direction of the fluid transfer direction) in the coordinate system shown in FIG. 1.

The reciprocation of the end 23 can be controlled by the waveform of the applied AC magnetic field 41.

For example, when the movement in the fluid transfer direction is defined as the outward movement and the movement in the direction opposite to the fluid transfer direction is defined as the homeward movement, the waveform of the AC magnetic field 41 can be set such that the transfer rate of the end 23 in the outward movement is greater than that in the homeward movement. Specifically, the waveform of the AC magnetic field 41 in the outward movement is set such that a relatively sharp magnetic gradient (a change in density of magnetic flux) is generated, so that the end 23 moves at a relatively high rate. In addition, the waveform of the AC magnetic field 41 in the homeward movement is set such that a relatively moderate magnetic gradient is generated, so that the end 23 moves at a relatively low rate.

By controlling the reciprocation of the end 23 such that the transfer rate in the outward movement is greater than that in the homeward movement, the magnetic body 20 moves as a pendulum using the fixed end 22 as the fulcrum to transfer the sample (functions as a nano-pump). This fluid-transferring effect allows the sample to circulate in the microcapillary tube 10 and the passage 11 in a predetermined direction.

FIG. 4 schematically shows the manner that the magnetic body 20 in a sample functions as a nano-pump. FIG. 4(A) is a view of the columnar magnetic body 20 viewed from a side, and FIG. 4(B) is a view of the columnar magnetic body 20 viewed from the above. The magnetic body 20 in each drawing is schematically illustrated, and, therefore, the size ratio is not limited to those shown in the drawings.

Furthermore, the difference in the reciprocation speed in the fluid transfer operation mode can be determined according to the type of the sample and the required fluid-transferring ability. When the fluid transfer effect is not necessary, the application of the AC magnetic field 41 may be terminated.

In the reaction apparatus 1 in Example 1, since the sample can be transferred by the movement of the magnetic body 20 in the sample, a pump in a conventional manner is unnecessary. Consequently, it is unnecessary that the sample has a volume for flowing in the piping of a pump, which is conventionally needed. As a result, the efficiency of sample use can be increased. In addition, the elimination of machinery, namely, the pump can avoid the shortening of the operating life of the apparatus due to breakdown or the like of the machinery.

Furthermore, since the magnetic bodies 20 serving as nano-pumps are dispersed in the sample in the microcapillary tube 10, the fluid transfer can be precisely controlled over the entire microcapillary tube 10. This allows the sample to smoothly flow in the microcapillary tube 10, resulting in shortening of the throughput time for completing the binding reaction.

In addition, since the sample is repeatedly brought into contact with the probe molecule 51 by circulating in the microcapillary tube 10 via the passage 11, the binding opportunity between the analyte 50 and the probe molecule 51 can be increased without increasing the volume of the sample fed into the reaction apparatus 1.

EXAMPLE 2

In Example 2, an increase in reaction efficiency is attempted by using the magnetic body 20 as a nano-pump and a nano-stirrer.

In Example 2, steps 1 to 4 are the same as those in Example 1. However, in Example 2, when the microcapillary tube 10 is filled with the sample, the end-moving means 32 is changed from step 4 to step 5 and vice versa described below, and both steps are repeated.

Specifically, in step 5, application of an AC magnetic field 42 in the stirring operation mode is performed by the end-moving means 32. The application direction and the magnitude of the AC magnetic field 42 in the stirring operation mode can be determined according to the type of the sample and the required stirring ability.

For example, the waveform of the AC magnetic field 42 can be set such that the direction of the magnetic field for the end 23 rotates 360° in a predetermined plane (for example, the X-Y plane in the coordinate system shown in FIG. 1) (see FIG. 3(C)). In this case, the end 23 of the magnetic body 20 moves approximately in a circle in the plane. As a result, the magnetic body 20 moves as a conical pendulum using the fixed end 22 as the fulcrum and thereby functions so as to stir the fluid (functions as a nano-stirrer).

FIG. 5 schematically shows the manner that the magnetic body 20 in a sample functions as a nano-stirrer. FIG. 5(A) is a view of the columnar magnetic body 20 viewed from a side, and FIG. 5(B) is a view of the columnar magnetic body 20 viewed from the above. The magnetic body 20 in each drawing is schematically illustrated, and, therefore, the size ratio is not limited to those shown in the drawings.

For example, the rotation speed of the magnetic field in the stirring operation mode can be determined according to the type of the sample and the required stirring ability. Furthermore, when the stirring operation is unnecessary, the application or the AC magnetic field 42 may be terminated. The execution times of step 4 and step 5 may be different from each other. Furthermore, each execution time may vary according to time elapsed.

The reaction apparatus 1 of Example 2 can exhibit the same effects as in Example 1. Furthermore, since the magnetic body 20 can be provided with a function as a nano-stirrer for stirring the sample in the microcapillary tube 10 by controlling the AC magnetic field 42 applied to the microcapillary tube 10, the binding opportunity between the analyte 50 and the probe molecule 51 can be increased without increasing the volume of the sample fed into the reaction apparatus 1.

The present invention is not limited to the above embodiment and can be variously modified for application. For example, in the above-mentioned embodiment, the AC magnetic fields 41 and 42 are uniformly applied to the entire microcapillary tube 10, but it may be configured such that an AC magnetic field is locally applied. Alternatively, it may be configured that an AC magnetic field is uniformly or locally applied to the passage 11, in addition to or instead of the microcapillary tube 10. That is, the magnetic body 20 disposed in the sample in the passage 11 can be provided with a function as a nano-pump or a nano-stirrer by applying a DC magnetic field in a direction approximately orthogonal to the fluid transfer direction of the passage 11 by the end-fixing means and applying an AC magnetic field in a direction according to the fluid transfer direction of the passage 11 by the end-moving means.

In the above-mentioned embodiment, Example 1 describes a mode in which the magnetic body 20 functions as a nano-pump, and Example 2 describes a mode in which the magnetic body 20 functions as a nano-pump and a nano-stirrer, but a mode in which the magnetic body 20 functions only as a nano-stirrer may be employed. In also such a case, by the function of the magnetic body 20 as a nano-stirrer and the circulation of the sample in the microcapillary tube 10 via the passage 11, the binding opportunity between the analyte 50 and the probe molecule 51 can be increased without increasing the volume of the sample fed into the reaction apparatus 1.

Furthermore, the reaction apparatus may have a structure for detecting the binding of an analyte in the microcapillary tube 10 or a structure including a unit for data processing of detection results. Exemplary embodiments of the process of detecting the binding include that using a light absorption observation device as in a known method and that determining the amount of the binding from a change in the impedance of the microcapillary tube 10.

Industrial Applicability

As described above, the reaction apparatus and process of the present invention can exhibit fluid-transferring and stirring functions by controlling the behavior of the magnetic body 20 in a sample and, therefore, can be broadly applied to various reaction apparatuses including capillaries.

BRIEF DESCRIPTION OF DRAWINGS

FIG. 4 includes diagrams illustrating a magnetic body 20 functioning as a nano-pump.

FIG. 5 includes diagrams illustrating a magnetic body 20 functioning as a nano-stirrer.

Figure 1:
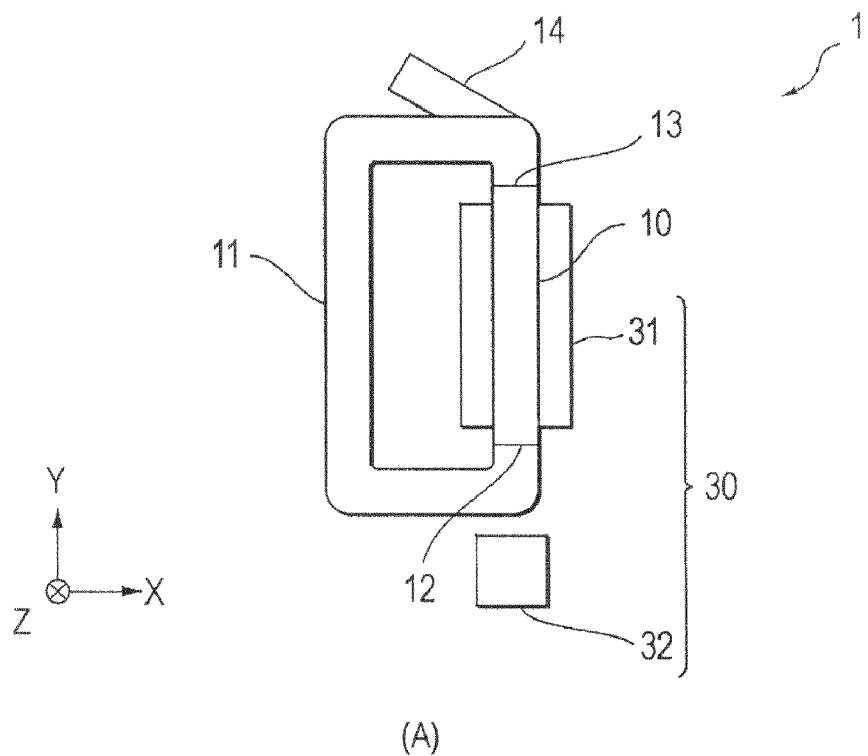
FIG. 1 includes diagrams schematically illustrating rough structures of a reaction apparatus 1 according to an embodiment of the present invention and a microcapillary tube 10 in the state that a sample is placed in the reaction apparatus 1.
Figure 1:
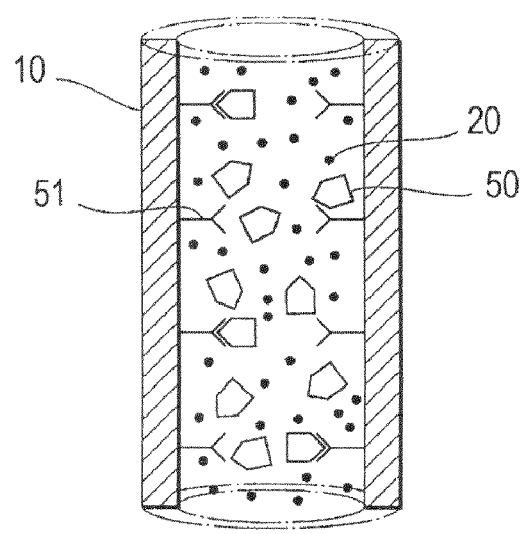
Figure 2:
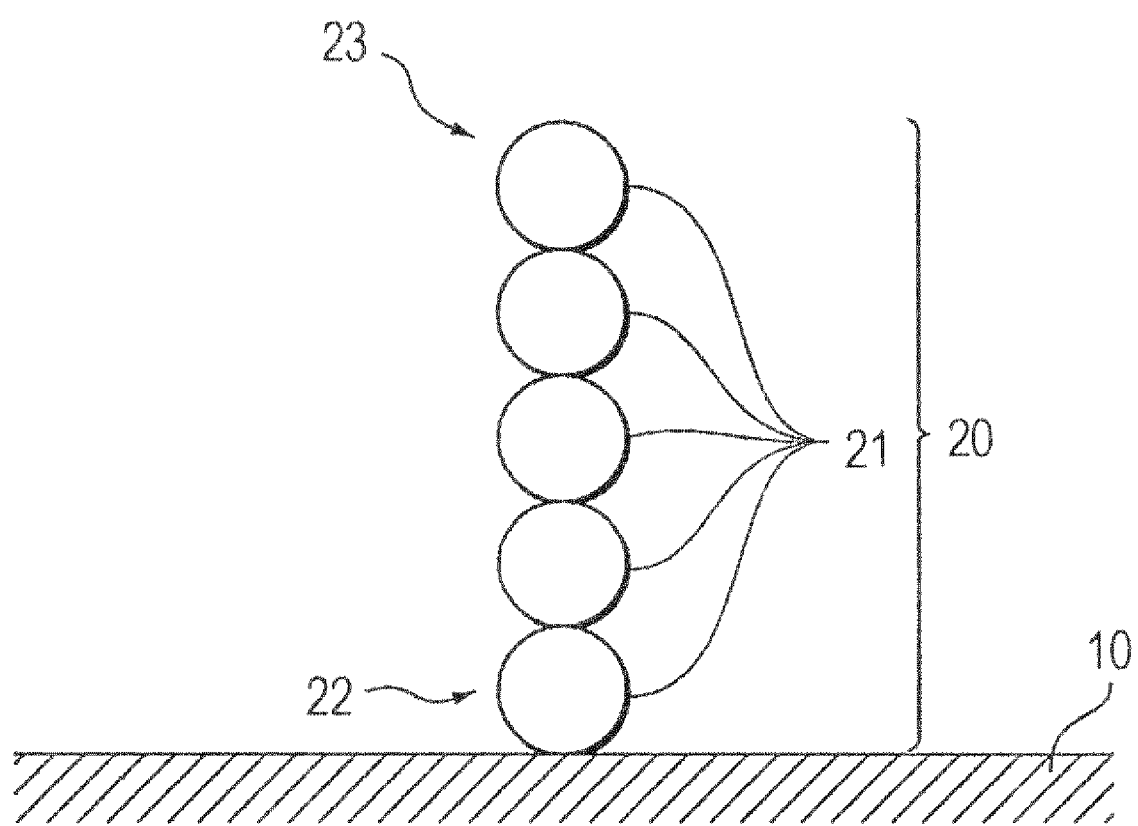
FIG. 2 is a diagram illustrating a magnetic body 20.
Figure 3:
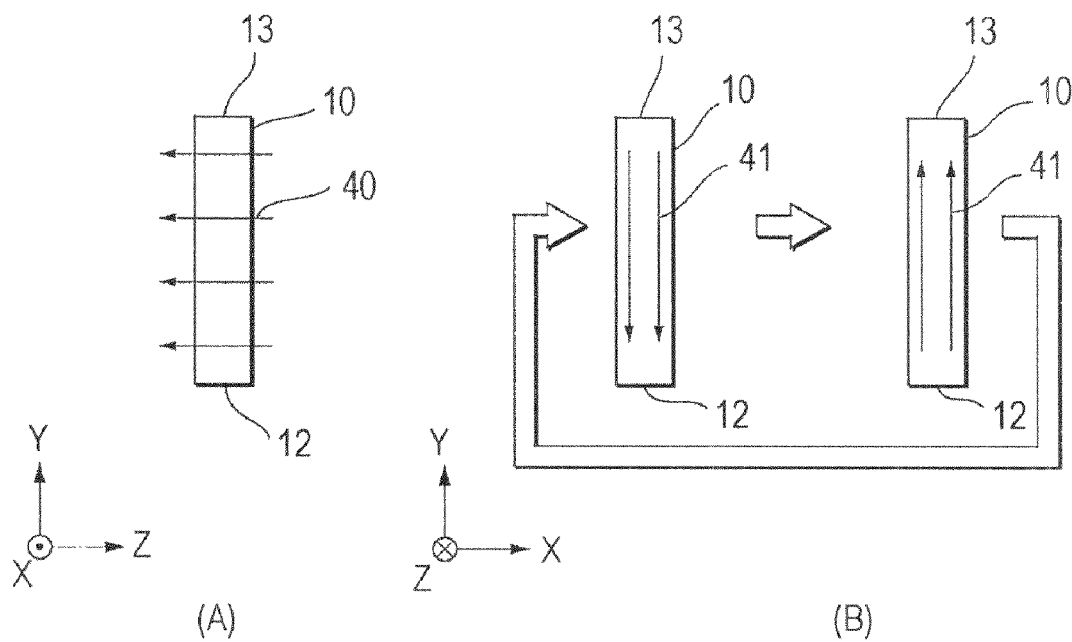
FIG. 3 includes diagrams illustrating a DC magnetic field 40 and AC magnetic fields 41 and 42 applied by end-fixing means 31 and end-moving means 32, respectively.
Figure 3:
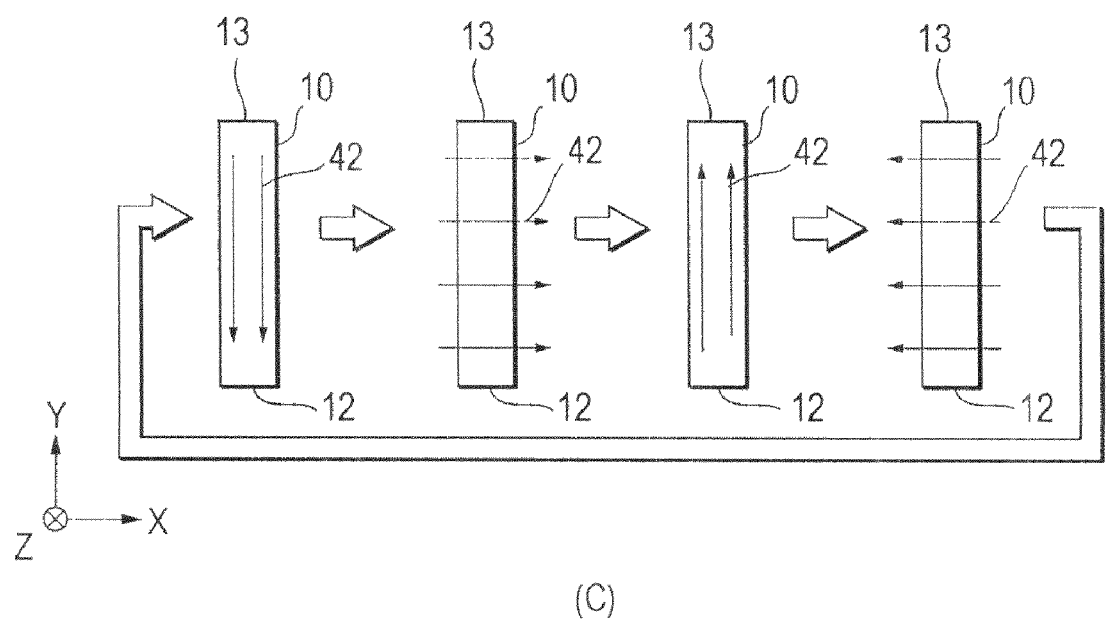

REFERENCE NUMERALS 1 reaction apparatus
10 microcapillary tube
11 passage
12 outlet end
13 inlet end
14 feeding channel
20 magnetic body
21 magnetic particle
22, 23 end of magnetic body 20
30 controller
31 end-fixing means
32 end-moving means
40 DC magnetic field
41, 42 AC magnetic field

The invention claimed is:

1. A reaction apparatus comprising:
a capillary having an inner surface to which a probe molecule that specifically binds to an analyte is immobilized;
a passage allowing a fluid discharged from one end of the capillary to flow to the other end of the capillary;
a columnar magnetic body that is disposed in a fluid containing the analyte in the capillary and/or the passage and configured to allow the fluid fed in the capillary to circulate via the passage;
end-fixing means for fixing one end of the columnar magnetic body in the capillary and or the passage using a DC magnetic field; and
end-moving means for moving the unfixed end of the columnar magnetic body using an AC magnetic field such that the fluid circulates via the passage.

2. The reaction apparatus according to claim 1, wherein the end-moving means applies an AC magnetic field in a direction approximately parallel to the fluid transfer direction to allow the unfixed end of the columnar magnetic body to reciprocate in the fluid transfer direction and the opposite direction such that the columnar magnetic body moves as a pendulum using the fixed end as the fulcrum.

3. The reaction apparatus according to claim 2, wherein the end-moving means allows the unfixed end to reciprocate at different rates in the fluid transfer direction and the opposite direction.

4. The reaction apparatus according to claim 1, wherein the end-moving means applies an AC magnetic field such that the direction of the magnetic field rotates 360° in a plane containing the capillary or the passage and allows the unfixed end of the columnar magnetic body to move approximately in a circle in the plane such that the columnar magnetic body moves such as a conical pendulum using the fixed end as the fulcrum.

5. The reaction apparatus according to claim 1, wherein the columnar magnetic body is formed by magnetically binding a plurality of magnetic particles in a columnar shape using the DC magnetic field.

6. A reaction process comprising the steps of:
contacting a fluid containing an analyte with a capillary having an inner surface to which a probe molecule that specifically binds to the analyte is immobilized;
fixing one end of a columnar magnetic body disposed in the fluid in the capillary using a DC magnetic field; and
moving the unfixed end of the columnar magnetic body using an AC magnetic field such that the fluid circulates via a passage connecting both ends of the capillary.

* * * * *

UNITED STATES PATENT AND TRADEMARK OFFICE
CERTIFICATE OF CORRECTION

| | | |
|---|---|---|
| PATENT NO. | : 8,377,708 B2 | Page 1 of 1 |
| APPLICATION NO. | : 12/665704 | |
| DATED | : February 19, 2013 | |
| INVENTOR(S) | : Sandhu | |

It is certified that error appears in the above-identified patent and that said Letters Patent is hereby corrected as shown below:

In the Specification

In Column 3, Line 4, delete "tubes" and insert -- tube --, therefor.

In Column 3, Line 38, delete "an RNA," and insert -- a RNA, --, therefor.

In Column 4, Line 27, delete "in" and insert -- as in --, therefor.

Signed and Sealed this
Fourth Day of June, 2013

Teresa Stanek Rea
*Acting Director of the United States Patent and Trademark Office*